(12) United States Patent
Gill et al.

(10) Patent No.: US 6,379,663 B1
(45) Date of Patent: *Apr. 30, 2002

(54) IMMUNITY ENHANCING LACTIC ACID BACTERIA

(75) Inventors: Harsharnjit S. Gill, Palmerston North; John B. Smart, Ashhurst; Pramod K. Gopal, Palmerston North, all of (NZ)

(73) Assignee: New Zealand Dairy Board, Wellington (NZ)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/485,875
(22) PCT Filed: Aug. 18, 1998
(86) PCT No.: PCT/NZ98/00122
    § 371 Date: Feb. 16, 2000
    § 102(e) Date: Feb. 16, 2000
(87) PCT Pub. No.: WO99/10476
    PCT Pub. Date: Mar. 4, 1999

(30) Foreign Application Priority Data

Aug. 21, 1997 (AU) .............................. PO 8699
Aug. 28, 1998 (AU) .............................. PP 3225

(51) Int. Cl.[7] ........................... A01N 63/00; C12N 1/20
(52) U.S. Cl. ................. 424/93.45; 435/252.9; 435/854
(58) Field of Search .................... 424/93.45; 435/252.9, 435/854

(56) References Cited

U.S. PATENT DOCUMENTS 5,164,183 A    11/1992  Komoda et al.
5,494,664 A  *  2/1996  Brassart et al.

FOREIGN PATENT DOCUMENTS

| | | | |
|---|---|---|---|
| EP | 0295794 B1 | | 5/1988 |
| JP | 09002959 | * | 1/1997 |
| NZ | 248057 | | 7/1993 |
| WO | WO 94/18997 | | 9/1994 |
| WO | WO 97/09448 | * | 3/1997 |
| WO | WO 98/23727 | | 6/1998 |

* cited by examiner

Primary Examiner—Christopher R. Tate
Assistant Examiner—Michele C. Flood
(74) Attorney, Agent, or Firm—Knobbe, Martens, Olson & Bear, LLP

(57) ABSTRACT

Novel bacteria *Lactobacillus rhamnosus* HN001 and HN 067, *Lactobacillus acidophilus* HN017, and *Bifidobacterium lactis* HN019 are claimed. Each strain provides immune enhancing effects when ingested.

12 Claims, 3 Drawing Sheets

US 6,379,663 B1

IMMUNITY ENHANCING LACTIC ACID BACTERIA

This is the U.S. National Phase under 35 U.S.C. § 371 of International Application PCT/NZ98/00122, filed Aug. 18, 1998 which claims priority of Australian Application Nos. AU PP 3225, filed Apr. 28, 1998 and AU PO 8699, filed Aug. 21, 1997.

TECHNICAL FIELD

This invention relates to novel strains of lactic acid bacteria and their use in enhancing immunity.

BACKGROUND ART

The consumption of products containing lactic acid bacteria (LAB) is associated with a range of health benefits including enhancement of immunity. There are thousands of strains of lactic acid bacteria but only some strains exhibit health-promoting properties. The ability of these bacteria to tolerate acids and bile salts, adhere to mucosal epithelial cells, and to survive passage through the gastrointestinal tract is considered an important criterion for selection of health-promoting strains. Only a few strains of lactic acid bacteria with proven health benefits have been identified to date.

Strains of LAB showing good adhesion to the cells of the mucosal epithelium of the small intestine thereby lending themselves to therapeutic applications are known from New Zealand Patent 248057. The micro-organisms described in this patent enhance both natural inununity (phagocyte function) and acquired immunity (antibody responses and lymphocyte proliferation responses).

It is desirable to have other LAB bacteria that enhance a broad spectrum of immune responses including phagocyte function.

It is an object of this invention to go some way towards achieving these desiderata or at least to offer the public a useful choice of immune enhancing lactic acid bacteria.

DISCLOSURE OF THE INVENTION

Accordingly, in one aspect the invention may be said broadly to consist of a biologically pure culture of *Lactobacillus rhamnosus* HN001, AGAL deposit number NM97/09514 dated Aug. 18, 1997.

In another aspect the invention may be said broadly to consist of a biologically pure culture of *Lactobacillus rhamnosus* HN067, AGAL deposit number NM97/01925 dated Feb. 17, 1998.

In another aspect the invention may be said broadly to consist of a composition of a biologically pure culture of any one of *Lactobacillus acidophilus* HN017, AGAL deposit number NM97/09515 dated Aug. 18, 1997, *Lactobacillus rhamnosus* HN001, *Lactobacillus rhamnosus* HN067 or *Bifidobacterium lactis* HN019, AGAL deposit number NM97/09513 dated Aug. 18, 1997 in an immunostimulating concentration, with a physiologically acceptable excipient or diluent.

In one embodiment said composition contains any two or more of said strains.

Preferably said physiologically acceptable excipient or diluent is a food.

Preferably said food is any one of cultured milk, yoghurt, cheese, milk drink or milk powder.

Alternatively said composition is a pharmaceutical composition and said excipient or diluent is pharmacologically acceptable excipient or diluent.

Immunity enhancing, physiologically acceptable, biologically pure strains of homologues or mutants of any one of the strains:

*Lactobacillus acidophilus* HN017,
*Lactobacillus rhamnosus* HN001,
*Bifidobacterium lactis* HN 019, or
*Lactobacillus rhamnosus* HN067.

In another embodiment the invention may be said broadly to consist of a method of enhancing natural and acquired immunity which comprises administering to a mammal any one of the above biologically pure cultures at an immunostimulating dosage rate.

In another embodiment substantially biologically pure cultures of two or three of the above-defined strains are present.

Preferably said culture is administered in the form of a composition with a physiologically acceptable excipient or diluent.

Preferably said physiologically acceptable excipient or diluent is a food.

Preferably said food is cultured milk, yoghurt, cheese, milk drink or milk powder.

This invention may also be said broadly to consist in the parts, elements and features referred to or indicated in the specification of the application, individually or collectively, and any or all combinations of any two or more of said parts, elements or features, and where specific integers are mentioned herein which have known equivalents in the art to which this invention relates, such known equivalents are deemed to be incorporated herein as if individually set forth.

MODES OF CARRYING OUT THE INVENTION

Figure 1:
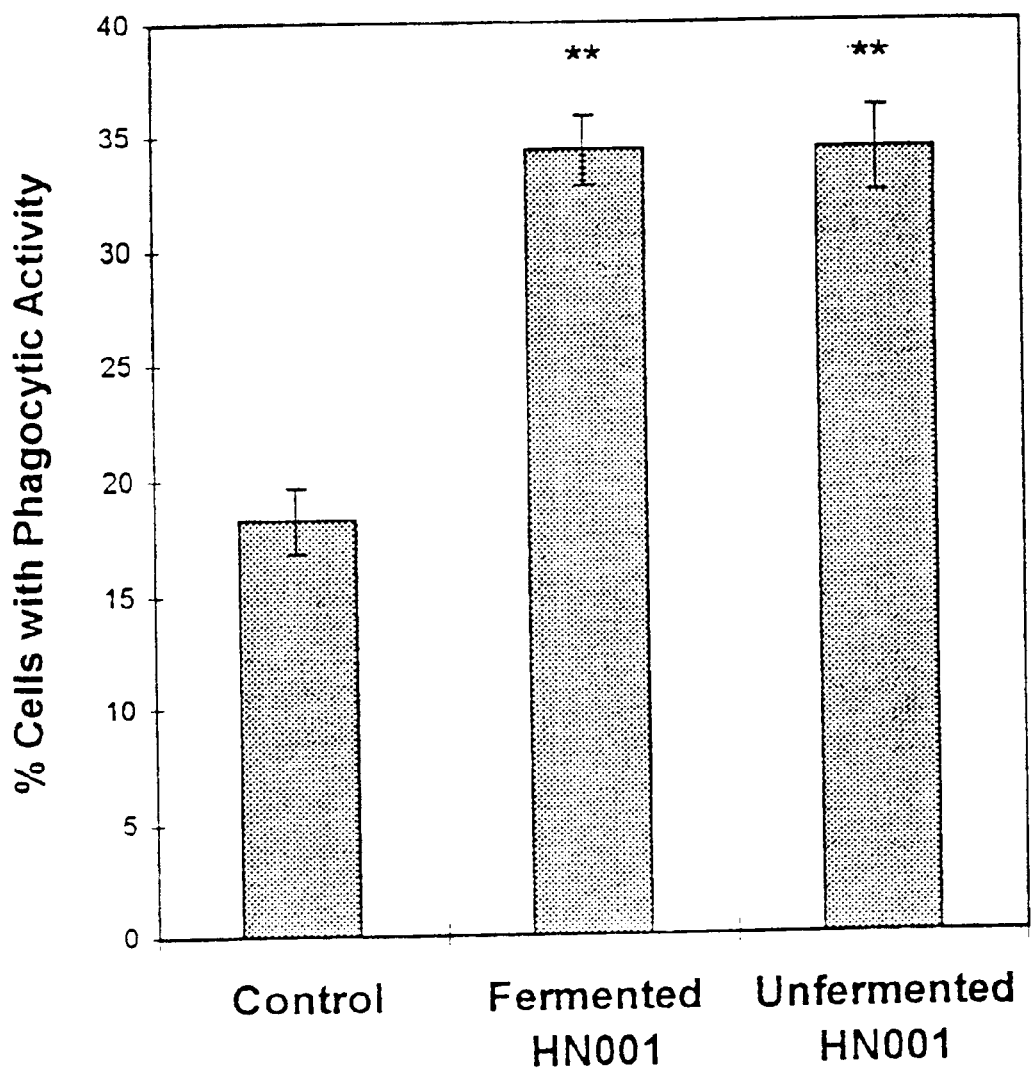
FIG. 1 shows the effect of supplementation of mice with product fermented with *L. rhamnosus* HN001 or unfermented product containing *L. rhamnosus* HN001 on phagocyte activity of peripheral blood leukocytes as described in example 5. BALB/c mice were fed on milk based diets containing $10^9$ cfa (per day) *L. rhamnosus* HN001 in either fermented or unfermented product for 14 days. Phagocytic activity of peripheral blood leukocytes was determined using flow cytometry and fluoroscein isothiocyanate-labelled *Escherichia coli*. Values are mean±standard error. Significant differences (ANOVA, the SAS program) from the control: **$P<0.0001$.

Freeze dried cultures of the four bacterial strains have been deposited at the Australian Government Analytical Laboratories (AGAL), The New South Wales Regional Laboratory, I Suakin Street, Pymble, NSW 2073, Australia. Details of the deposits are:

| Strain | Number | Date |
| --- | --- | --- |
| *L. acidophilus* HN017 | NM97/09515 | August 18, 1997 |
| *L. rhamnosus* HN001 | NM97/09514 | August 18, 1997 |
| *B. lactis* HN019 | NM97/09513 | August 18, 1997 |
| *L. rhamnosus* HN067 | NM97/01925 | February 11, 1998 |

The four strains identified above have been found to enhance a broad spectrum of immune responses including both natural and acquired immune responses.

EXAMPLE 1

Morphology and General Properties

RAPD analysis, 16S rRNA sequencing and SDS-PAGE analyses were used to confirm taxonornical characterisation of strains. It was also found that *L. acidophilus* HN017 was genetically different from *L. acidophilus* (LC1) of New Zealand Patent No. 248057.

RAPD analysis, 16S rRNA sequencing and SDS-PAGE analyses were used to confirm taxonomical characterisation of *L. rhamnosus* HN067; species-specific primers used for characterisation of *L. rhamnosus* HN067 at molecular level included Pr I (forward) 5-CAGACTGAAAGTCTGACGG-3 and Pha II (reverse) 5-GCGATGCGAATTTCTATTATT-3.

The morphology and sugar fermentation properties of this strain are detailed in Tables 1 and 2.

TABLE 1

Morphology and other characteristics

| *L. acidophilus* HN017 | *L. rhamnosus* HN001 | *B. lactis* HN019 | *L rhamnosus* HN067 |
| --- | --- | --- | --- |
| Short to medium rods with rounded ends, generally occurring singly or in pairs or short chains, when grown in MRS broth. Gram positive, non-spore forming, catalase negative facultatively anaerobic rods with optimum growth temperature of 37 ± 1° C. and optimum pH of 6.0–6.5. These are obligately homofermentative | Short to medium rods with square ends in chains, generally 0.7 × 1.1 × 2.0–4.0 μm, when grown in MRS broth. Gram positive, non-mobile, non-spore forming, catalase negative facultative anaerobic rods with optimum growth temperature of 37 ± 1° C. and optimum pH of 6.0–6.5. These are facultatively heterofermentative bacteria and no | Microaerophilic to anaerobic rods with characteristic shapes such as middle enlarged cells, 'V' or palisade arrangement of cells when grown on TPY agar slabs. In MR5 broth with 0.05% cysteine hydrochloride, they form middle-enlarged cells and club shaped (spatulated extremities) cells. Gram positive, non-motile and non-spore forming, catalase negative rods with optimum growth temperature of 37 ± 1° C. and optimum | Short to medium rods with square ends in chains, generally 0.7 × 1.1 × 2.0 to 4.0 μm, when grown in MRS broth. Gram positive, catalase negative, non-mobile, non-spore-forming, facultative anaerobic rods with optimum growth temperature of 37 ± 1° C. and optimum pH of 6.0 to 6.5. These are facultatively heterofermentative bacteria and no gas produced from |

TABLE 1-continued

Morphology and other characteristics

| L. acidophilus HN017 | L. rhamnosus HN001 | B. lactis HN019 | L rhamnosus HN067 |
|---|---|---|---|
| bacteria and no gas is produced from glucose. | gas produced from glucose. | pH of 6.0–7.0. Fructose-6-phosphate phospho-ketolase positive. | glucose. |

TABLE 2

Carbohydrate fermentation pattern of selected Lactobacillus and Bifidobacterium strains

| S1. No. | Name of the bacterium | Score* |
|---|---|---|
| 1 | L. acidophilus HN017 | 5755546 |
| 2 | L. rhamnosus HN001 | 5757177 |
| 3 | B. lactis HN019 | 1051622 |
| 4 | L. rhamnosus HN067 | 5757175 |

API 50 CH sugar fermentation kit was used to determine the sugar-fermentation pattern.
*The scores are based on scores of 22 prominent sugars (Bergey's manual)

EXAMPLE 2

Adhesion to Intestinal Cells

The ability of probiotic strains to adhere to human intestinal epithelial cells (HT-29 and CaCo-2) was assessed in vitro using differentiated cell-lines. Monolayers of HT-29 and CaCo-2 cells were grown on cover slips and placed in multi-well dishes. $10^8$ cfu/ml of LAB in 1 ml of spent culture supernatant was then added to cell layers along with 1 ml of DMEM medium and incubated for 1 hr at 37° C. in 10% $CO_2$-90% air. Monolayers were washed 4 times with PBS, fixed in methanol, Gram strained and the number of bacteria adhering to epithelial cells determined microscopically. On average, 20 fields were counted and the results are summarised in Table 3.

TABLE 3

Adherence to HT-29 and CaCo-2 cell lines*

| STRAIN | HT-29 | CaCo-2 |
|---|---|---|
| L. acidophilus HN017 | 98 ± 17 | 171 ± 16 |
| L. rhamnosus HN001 | 161 ± 18 | 218 ± 35 |
| B. lactis HN019 | 188 ± 27 | 194 ± 25 |

*Number (mean ± SEM) of bacteria/100 epithelial cells

EXAMPLE 3

Enhancement of Natural and Acquired Immunity

The immunoenhancing effects of the three strains L. rhamnosus HN001, L. acidophilus HN017 and B. lactis HN019 were examined by determining phagocyte (blood leukocytes and peritoneal macrophage) function, and quantifying concentrations of specific antibodies to protein antigens used for mimicking responses to vaccines in mice.

The following experimental protocol was used:

1. Six-to-seven week old BALBIc mice, weighing 20–30 g were used.
2. Mice were randomly allocated to different treatment groups (Table 4)
3. Mice were fed L. acidophilus HN017, L. rhamnosus HN001 or B. lactis HN019 ($10^9$ cfu/day) in 50 µl skim milk for 10 days. Control mice received 50 µl of skim milk powder only.
4. All mice received skim milk powder based diet throughout the experiment.

Blood leukocytes and macrophages from mice receiving L. acidophilus HN017, L. rhamnosus HN001 or B. lactis HN019 showed significantly greater phagocytic capacity compared with cells from control mice (Table 4). The production of oxygen radicals (oxidative burst) by leukocytes from probiotic fed mice was also higher than the control mice (data not shown).

TABLE 4

The effect of dietary L. acidophilus HN017, L. rhamnosus HN001 and B. lactis HN019 on phagocyte function in mice

| Treatment | % Blood leukocytes with phagocytic activity | % Peritoneal macrophage with phagocyte activity |
|---|---|---|
| Control | 14.33 ± 0.87 | 66.1 ± 3.5 |
| L. acidophihilus HN017 | 22.7 ± 1.21** | 79.0 ± 1.0** |
| L. rhamnosus HN001 | 24.84 ± 0.93** | 0.5 ± 1.8** |
| B. lactis HN019 | 23.19 ± 0.95** | 77.4 ± 2.6* |

BALB/c mice were orally administered with $10^9$ cfu (per day) L. acidophilus HN017, L. rhamnosus HN001 or B. lactis HN019 for 10 days. Phagocytic activity of blood leukocytes and peritoneal macrophages was determined using flow cytometry and fluorescein isothiocyanate—labelled Escherichia coli. Values are mean±standard error. Significant differences (Students t test) from the control: *P<0.05, **P<0.01.

The concentration of specific IgG antibodies in the sera and in the intestinal washings of mice receiving L. acidophilus HN017, L. rhamnosus HN001 or B. lactis HN019 was also greater than those of control mice (Table 5).

TABLE 5

The effect of dietary L. acidophilus HN017, L. rhamnosus HN001 and B. lactis HN019 on serum and mucosal antibody responses

| Treatment | Serum antibody response (units/ml) | Mucosal antibody response (units/ml) |
|---|---|---|
| Control | 80.2 ± 6.0 | 1350 ± 96.0 |

TABLE 5-continued

The effect of dietary L. acidophilus HN017, L. rhamnosus HN001 and B. lactis HN019 on serum and mucosal antibody responses

| Treatment | Serum antibody response (units/ml) | Mucosal antibody response (units/ml) |
|---|---|---|
| L. acidophilus HN017 | 134.6 ± 25.2* | 1548 ± 270.0 |
| L. rhamnosus HN001 | 118.5 ± 12.5** | 1512 ± 198.0 |
| B. lactis HN019 | 158.1 ± 51.6*** | 1548 ± 234.0 |

BALB/c mice were orally administered with $10^9$ cfu (per day) L. acidophilus HN017, L. rhamnosus HN001 or B. lactis HN019 for 10 days. Mice were immunised with cholera toxin (an antigen used to mimic enteric infection) on days 0 and 7. The concentration of specific antibodies in serum and intestinal secretions were measured using ELISA on day 10. Values represent mean±standard error. Significant differences (Students t test) from control: *P=0.08; P<0.05; *P<0.01.

EXAMPLE 4

Immunostimulating Effects Following Supplementation with LAB for Four Weeks

The immunostimulating effects of L. acidophilus HN017, L. rhamnosus HN001, and B. lactis HN019 were assessed in mice using the following experimental protocol:

1. Six-to-seven week old BALB/c mice, weighing 20–30 g were used.
2. Mice were randomly allocated (18/group) to different treatment groups.
3. After acclimatisation (for 7 days), mice were given $10^9$ cfu (per day) L. acidophilus HN017, L. rhamnosus HN001, or B. lactis HN019, in 50 µl skim milk, for 28 days (from day 0 to day 28). Control mice received 50 µl skim milk (without any micro-organisms) only.
4. Mice were offered a skim milk powder based-diet and water ad libitum, throughout the experiment.
5. Immunostimulating effects were assessed by monitoring phagocytic activity of blood leukocytes and peritoneal macrophages, NK-cell activity of splenic lymphocytes, lymphocyte proliferation (spleen cells) responses to a T-cell mitogen, ConA (an indicator of cell-mediated immunity) and antibody responses to Tetanus vaccine.

As seen in Table 6, leukocytes (neutrophils, monocytes and macrophages) from mice receiving L. acidophilus HN017, L. rhamnosus HN001, or B. lactis HN019 exhibited significantly greater phagocytic activity (an indicator of natural immunity) than leukocytes from control mice.

TABLE 6

The effect of dietary L. acidophilus HN017, L. rhamnosus HN001, and B. lactis HN019 in mice

| Treatment | % Blood leukocytes with phagocytic activity | % Peritoneal macrophages with phagocytic activity |
|---|---|---|
| Control | 15.5 | 72.67 |
| L. acidophilus HN017 | 29.4** | 82.2* |
| L. rhamnosus HN001 | 24.2** | 82.8** |
| B. lactis HN019 | 31.1** | 83.0** |

Mice (18/group) were given $10^9$ cfu (per day) L. acidophilus HN017, L. rhamnosus HN001, or B. lactis HN019 in 50 µl skim milk for 28 days. Phagocytic activity of blood leukocytes/peritoneal macrophages was determined on day 28 using flow cytometry and fluorescein isothiocyanate-labelled E. coli. Values are least square means. Significant differences (the SAS analysis): *P<0.002, **P<0.0005.

Consumption of L. acidophilus HN017, L. rhamnosus HN001, or B. lactis HN019 for 28 days also resulted in an increase in the NK-cell activity, lymphocyte proliferation responses to ConA and antibody responses to Tetanus vaccine. For all these indicators of immunocompetence, mice receiving L. acidophilus NN017, L. rhamnosus HN001, or B. lactis HN019 had higher responses than those of control mice (Table 7).

Together these results show that supplementation for extended periods with L. acidophilus HN017, L. rhamnosus HN001, or B. lactis HN019 is able to induce a sustained enhancement in several aspects of natural and acquired immunity.

TABLE 7

The effect of dietary L. acidophilus HN017, L. rhamnosus HN001, and B. lactis HN019 on NK cell activity and lymphocyte proliferation responses to ConA and antibody responses to Tetanus vaccine.

| ConA Treatment | NK cell activity (%) | Lymphocyte proliferation to ConA (absorbance) | Antibody responses to Tetanus vaccine (units/ml) |
|---|---|---|---|
| Control | 8.8 | 1.4 ± 0.125 | 402.5 ± 41.4 |
| L. acidophilus HN017 | 9.9 | 1.6 ± 0.44 | 923.9 ± 116.0* |
| L. rhamnosus HN001 | 11.5 | 1.8 ± 0.1* | 711.5 ± 127.2* |
| B. lactis HN019 | 10.5 | 1.7 ± 0.5 | 844.6 ± 134.7* |

Mice (18/group) were given $10^9$ cfu (per day) L. acidophilus HN017, L. rhamnosus HN001, or B. lactis HN019 in 50 µl skim milk for 28 days (i.e. from days 0 to 28). NK-cell activity of splenic lymphocytes was determined on day 28 using flow cytometry and D275-labelled Yac-1 cells. Lymphocyte proliferation responses of splenic lymphocytes to ConA were assessed on day 28 using a commercial cell proliferation kit (Boehringer Mannheim, Germany). For antibody responses, mice were immunised with Tetanus vaccine (50 µl/dose, CSL, Australia) on days 7 and 21. The concentration of specific antibodies were determined using an ELISA; antigen supplied by the vaccine manufacturers (CSL, Australia) was used for coating plates. Values are least square means of 18 mice. Significant differences (the SAS analysis): *P <0.05.

EXAMPLE 5

Enhancement of Natural and Acquired Immunity Using Fermented Versus Unfermented Products The aim was to assess the immunoenhancing efficacy of yoghurt made (fermented) using the probiotic strain L.

rhamnosus HN001 compared to unfermented product containing *L. rhamnosus* HN001. The immunoenhancing effects were examined by determining the phagocyte function (peripheral blood leukocytes and peritoneal macrophages) and lymphocyte proliferative responses to a B-cell mitogen (LPS).

The following experimental protocol was used:
1. Six-to-seven week old BALB/c mice, weighing 20–30 g were used.
2. Mice were randomly allocated to different treatment groups.
3. Control mice received a whole milk powder-based diet throughout the experiment.
4. Test mice received 2.5 g yoghurt made using *L. rhamnosus* HN001 ($10^9$ cfu/day) or 2.5 g whole milk containing *L. rhamnosus* HN001 ($10^9$ cfu/day) per day as well as a whole milk powder based diet for 14 days.

Results

Mice receiving yoghurt made with *L. rhamnosus* HN001 or whole milk containing *L. rhamnosus* HN001 displayed a significantly higher level of phagocytic activity of peripheral blood leukocytes than was observed in mice receiving the control diet (FIG. 1). This increase was seen irrespective of whether the *L. rhamnosus* HN001 was delivered in the yoghurt (fermented with *L. rhamnosus* HN001) or unfermented product containing *L. rhamnosus* HN001. There was no difference in the level of phagocytic activity between mice receiving the fermented yoghurt made using *L. rhamnosus* (HN001) compared to unfermented WMP product containing *L. rhamnosus* (HN001).

Both the unfermented and *L. rhamnosus* HN001 fermented product fed mice showed higher lymphocyte proliferative responses to LPS than the control mice (Table 8). There was no significant difference in the response between mice receiving unfermented product containing *L. rhamnosus* HN001 and mice receiving product fermented with *L. rhamnosus* HN001.

TABLE 8

The effect of fermented and unfermented *L. rhamnosus* HN001 on lymphocyte proliferative responses in mice

| Treatment | Lymphocyte proliferation to LPS (absorbance) |
|---|---|
| Control (WMP) | 0.4699 ± 0.028 |
| WMP Fermented with *L. rhamnosus* HN001 | 0.5361 ± 0.028 |
| Unfermented WMP with *L. rhamnosus* HN001 | 0.5518 ± 0.028* |

BALB/c mice were fed on milk based diets containing $10^9$ cfu (per day) *L. rhamnosus* HN001 in either unfermented product or yoghurt made with *L. rhamnosus* HN001 (fermented product) for 14 days. Control mice received milk-based diet without any LAB. Proliferative responses were measured colourimetrically following the incorporation of 5-bromo-2'-deoxyuridine for the final 16 hrs of the 96 hr incubation.

Values are means±standard error. Significant differences (Students t test) from the control: *P=0.05.

Together these results suggest that supplementation with *L. rhamnosus* HN001 enhances a range of immune functions including phagocytic activity and lymphocyte cell proliferation. *L. rhamnosus* HN001 presented in either fermented or unfermented product is effective at eliciting enhancement of immune function, with fermented product giving a greater response for some functions and unfermented being superior in others.

EXAMPLE 6

Enhancement of Natural and Acquired Immunity by *L. rhamnosus* HN067

Experiment 1.

The immunoenhancing effects of *L. rhamnosus* HN067 were examined by monitoring phagocytic capacity of peripheral blood leukocytes and peritoneal macrophages (indicator of non-specific immunity), and quantifying concentrations of specific antibodies to an immunisation antigen, cholera toxin (used for mimicking responses to enteric vaccines) in mice.

The following experimental protocol was used:
1. Six-to-seven week old BALB/c mice, weighing 20–30 g were used. They were fed on a skim milk-based diet throughout the experiment.
2. Mice in the test group (n=6) were orally administered *L. rhamnosus* HN067 ($10^9$ cfu/day) in 50 μl skim milk for 10 days. Control mice (n=6) received 50 μl of skim milk powder (without any LAB) only.

Results

Blood leukocytes and peritoneal macrophages from mice receiving *L. rhamnosus* HN067 showed significantly greater phagocytic activity (enhanced phagocyte function) compared with cells from control mice. The results are set out in Table 9 below.

TABLE 9

The effect of dietary *L. rhamnosus* HN067 on phagocyte function

| Treatment | % Blood leukocytes with phagocylic activity | % Peritoneal macrophages with phagocytic activity |
|---|---|---|
| Control | 13.1 ± 1.5 | 76.4 ± 1.9 |
| *L. rhamnosus* HN067 | 23.7 ± 1.5** | 87.2 ± 1.9* |

BALBlc mice (6/group) were fed on milk-based diet with or without oral administration of L. rhamnosus HN067 ($10^9$ cfu/day) for 10 days. Phagocytic activity of blood leukocytes and peritoneal macrophages were determined using flow cytometry and fluorescein isothiocyanate—labelled *E. coli*. Values represent least square mean±standard error LSM. Significant differences (the SAS program) from the control: *P=0.0005, **P=0.0001.

The concentration of specific antibodies to cholera toxin, an antigen used for oral immunisation, in the sera and in the intestinal washings of mice receiving *L. rhamnosus* HN067 was also significantly greater than those of control mice (Table 10).

TABLE 10

The effect of dietary supplementation with *L. rhamnosus* HN067 on serum and mucosal antibody responses to cholera toxin

| Treatment | Serum antibody response (units/ml) | Mucosal antibody response (units/ml) |
|---|---|---|
| Control | 63.1 ± 43.2 | 1969.7 ± 279.5 |
| *L. rhamnosus* HN067 | 246.5 ± 43.2** | 2995.5 ± 465.2* |

BALB/c mice were fed on milk-based diet with or without *L. rhamnosus* HN067 ($10^9$ cfu/day) for 10 days. Mice were immunised orally with cholera toxin (10 μg/dose), an antigen used to mimic enteric infection, on days 0 and 7. Antibody levels in serum and intestinal secretions were measured using ELISA on day 10. Values represent least square mean±standard error LSM. Significant differences (the SAS program) from control: *P=0.02; **P=0.0039.

Experiment 2.

The immunostimulating effects of *L. rhamnosus* HN067 were assessed in mice using the following experimental protocol:

1. Six-to-seven week old BALB/c mice, weighing 20–30 g were used. They were offered skim milk powder based diet and water ad libitum, throughout the experiment.
2. After acclimatisation for 7 days, mice in group 1 (n=20) were orally administered with $10^9$ cfu (per day) *L. rhamnosus* (HN067) in 50 μl skim milk (group 1 n=20) for 14 days. Control mice (group 2, n=20) received skim milk without any microorganisms.
3. Immunostimulating effects were assessed by monitoring phagocytic activity of blood leukocytes and peritoneal macrophages, and spleen lymphocyte proliferation responses to phytohaemagglutinin (PHA) and lipopolysaccharide (LPS) (T and B-cell mitogens respectively).

Results

Blood leukocytes and peritoneal macrophages from mice receiving *L. rhamnosus* HN067 exhibited significantly greater phagocytic activity (an indicator of natural immunity) than leukocytes and macrophages from control mice (Table 11).

TABLE 11

The effect of dietary *L. rhamnosus* HN067 on phagocyte function in mice

| Treatment | % Blood Leukocytes with phagocytic activity | % Peritoneal macrophages with phagocytic activity |
|---|---|---|
| Control | 13.7 ± 0.07 | 64.6 ± 2.1 |
| *L. rhamnosus* HN067 | 22.5 ± 0.07** | 75.8 ± 1.7* |

BALB/c mice were fed on milk-based diet with or without oral administration of *L. rhamnosus* HN067 ($10^9$ cfu/day) for 14 days. Phagocytic activity of blood leukocytes/peritoneal macrophages were determined on day 14 using flow cytometry and fluorescein isothiocyanate-labelled *E. coli*. Values represent least square mean±standard error LSM. Significant differences (the SAS program): *P=0.002, **P=0.0001.

Mice receiving *L. rhamnosus* HN067 for 14 days also displayed higher lymphocyte proliferation responses to PHA and LPS compared with control mice (Table 12).

TABLE 12

The effect of *L. rhamnosus* HN067 supplementation on lymphocyte proliferation responses to PHA and LPS

| ConA Treatment | Lymphocyte proliferation to PHA | Lymphocyte proliferation to LPS |
|---|---|---|
| Control | 1.18 ± 0.08 | 0.99 ± 0.07 |
| *L. rhamnosus* HN067 | 1.37 ± 0.07* | 1.24 ± 0.06** |

BALB/c mice were fed on milk-based diet with or without oral administration of *L. rhamnosus* HN067 ($10^9$ cfu/day) for 14 days. Lymphocyte proliferation responses of spleen cells to PHA and LPS were assessed on day 14 using a commercial cell proliferation kit (Boehringer Mannheim, Germany). Values represent least square mean±standard error LSM. Significant differences (the SAS program): *P<0.08, **P<0.01.

In summary, mice receiving *L. rhamnosus* HN067 displayed significant enhancement of a range of host immune responses including leukocyte phagocytic function, antibody responses to oral immunisation, and lymphocyte proliferation responses to T and B-cell mitogens. Blood leukocytes (neutrophils and monocytes) and macrophages are major effectors of natural immunity and play a major role in protection against microbial infections. A correlation between in vitro lymphocyte proliferation responses to mitogens (T- and B-cell mitogens) and immunocompetence of an individual is also well documented. Therefore, these results suggest that supplementation with *L. rhamnosus* HN067 is able to enhance several aspects of natural and acquired immunity.

EXAMPLE 7

Enhancement of Natural and Acquired Immunity Using Live and Heat Killed *L. rhamnosus* HN001

The aim of the present study was to investigate the immunoenhancing effects of the probiotic strain *L. rhamnosus* HN001 when presented in either the live or heat killed form. The effect on immune function was assessed by determining phagocytic activity of peripheral blood leukocytes. The effect of live and heat killed *L. rhamnosus* HN001 on humoral immunity was investigated by immunising mice with cholera toxin, and measuring the concentrations of specific antibodies produced.

The following experimental protocol was used:

1. Six-to-seven week old BALB/c mice, weighing 20–30 g were used.
2. Mice were randomly allocated to different treatment groups.
3. Control mice received a skim milk powder based diet throughout the experiment.
4. Test mice receive either $10^9$ cfu/day of live *L. rhamnosus* HN001 or $10^9$ cfu/day heat killed *L. rhamnosus* HN001 per day as well as a skim milk powder-based diet for 14 days.
5. Mice were orally immunised with cholera toxin on day 0 and day 7 of feeding.

Results

Figure 2:
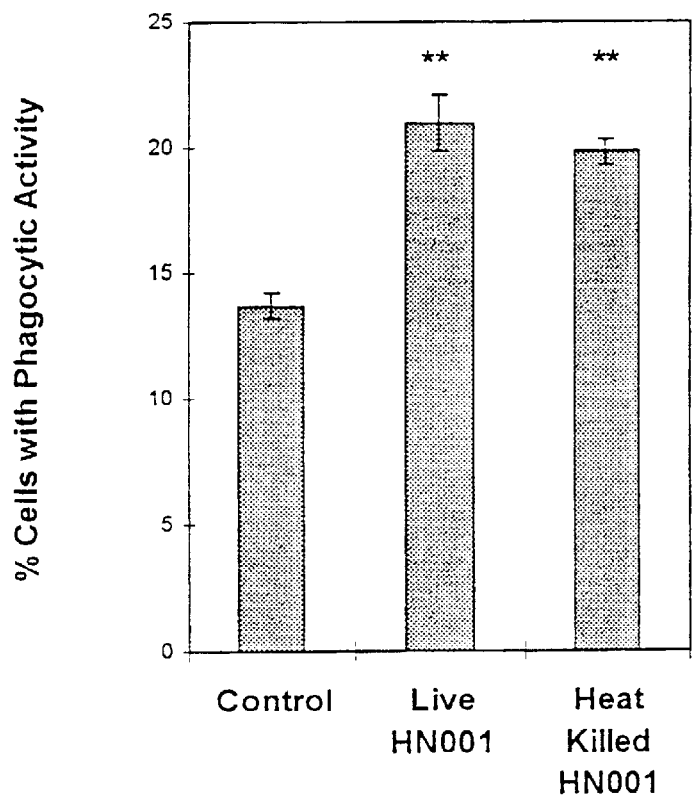
FIG. 2 shows the effect of supplementation of mice with live *L. rhamnosus* HN001 or heat killed L. rhamnosuis HN001 on phagocytic activity of peripheral blood leukocytes as described in example 7. BALB/c mice were fed on milk based diets and orally administered $10^9$ cfu (per day) of either live or heat killed *L. rhamnosus* HN001 for 14 days. Phagocytic activity of peripheral blood leukocytes and peritoneal macrophages were determined using flow cytometry and fluoroscein isothiocyanate—labelled *Escherichia coli*. Values are mean±standard error. Significant differences (ANOVA, the SAS program) from the control, **$P<0.0001$.

*L. rhamnosus* HN001 feeding significantly enhanced the level of phagocytic activity of peripheral blood leukocytes compared to mice receiving the control diet (FIG. 2). This increase was seen irrespective of whether the *L. rhamnosus* HN001 was delivered in the live or heat killed form. There was no difference in the level of phagocytic activity between the mice receiving live *L. rhamnosus* HN001 compared to heat killed *L. rhamnosus* HN001.

Feeding of both live and dead *L. rhamnosus* HN001 induced an increase in both serum and mucosal antibody responses compared to the control mice. However, the level of response was significantly greater in the mice fed the live *L. rhamnosus* HN001 (Table 13).

TABLE 13

The effect of live and heat killed *L. rhamnosus* HN001 on serum and mucosal antibody responses to Cholera Toxin in mice

| Treatment | Serum antibody response (units/ml) | Mucosal antibody response (units/ml) |
| --- | --- | --- |
| Control | 88.69 ± 18.52 | 708.6 ± 146.9 |
| Live *L. rhamnosus* HN001 | 214.89 ± 62.33* | 2054.5 ± 285.8*** |
| Heat Killed *L. rhamnosus* HN001 | 174.89 ± 44.78 | 1533.6 ± 319.3 |

BALB/c mice were fed on milk-based diets and orally administered $10^9$ cfu (per day) *L. rhamnosus* HN001 in either live or heat killed form for 14 days. Control mice received no LAB. Mice were orally immunised with Cholera Toxin on days 0 and 7. Antibody responses (serum and intestinal secretions) were measured using an ELISA on day 14. Values are mean±standard error. Significant differences (Students t test) from the control: *P=0.05, ***P=0.0005.

These results suggest that both live and heat killed *L. rhamnosus* HN001 are able to enhance aspects of natural and acquired immunity in mice.

EXAMPLE 8

Anti-infection properties of *B. lactis* HN019 and *L. rhamnosus* HN001

The aims of the current study were to:
1. Assess the protection efficacy of *B. lactis* HN019 and *L. rhamnosus* HN001 against the gastrointestinal pathogen *Salmonella typhimutrum*.
2. Determine the role of immunostimulation induced by *B. lactis* HN019 and *L. rhamnosus* HN001 in protection against *S. typhimurium* infection in mice.

Anti-infection properties were assessed by measurement of bacterial translocation to the liver and spleen. The immunoenhancing effects were examined by determining the phagocyte function (peripheral blood leukocytes and peritoneal macrophages) and lymphocyte proliferative responses to a T-cell mitogen (PHA).

The following experimental protocol was used:
1. Six-to-seven week old BALBIc mice, weighing 20–30 g were used.
2. Mice were randomly allocated to 4 difference treatment groups and were individually housed.
3. Al mice received a skim milk powder based diet throughout the experiment.
4. Test mice commenced daily feeding of *B. lactis* HN019 or *L. rhamnosus* HN001 ($10^9$ cfu/day) 7 days prior to challenge, and continued for the duration of the trial.
5. Mice administered with *B. lactis* HN019 or *L. rhamnosus* HN001 and a control group (no LAB) were orally challenged with *Salmonella typhimurium* (ATCC 1772) $8 \times 10^5$ cfu/day for 5 days starting on day 7.
6. An uninfected control group did not receive *S. typhimurium* challenge.
7. On day 6 after challenge mice were used for the measurement of bacterial translocation to the liver and spleen, and for immune function assessment.

Results

Figure 3:
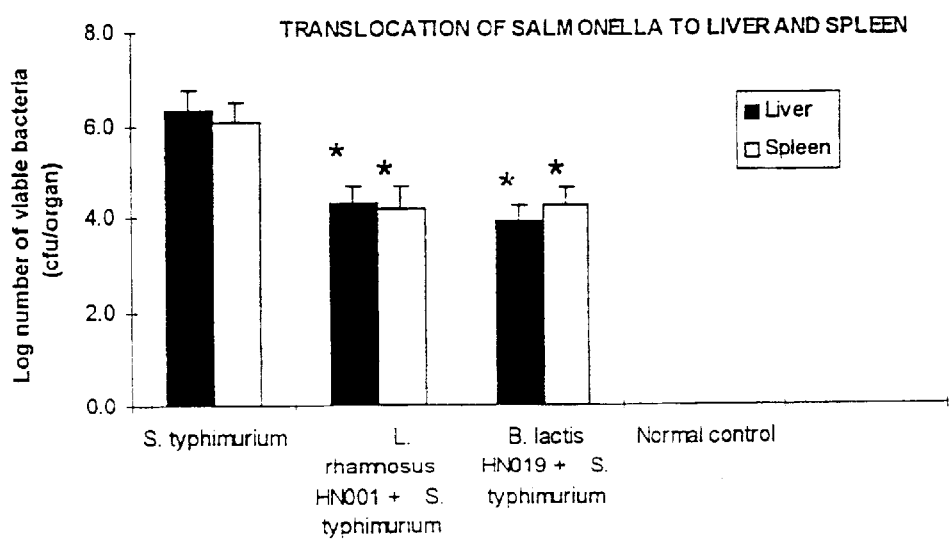
FIG. 3 shows the effect of supplementation of mice with *L. rhamnosus* HN001 or *B. lactis* HN019 on bacteria translocation in mice challenged with *S. typhimurium* as described in example 8. Unsupplemented and *B. lactis* HN019, or *L. rhamnosus* HN001 supplemented BALB/c mice were orally challenged with *S. typhimurium* following continuous daily supplementation. Six days after challenge mice were humanely killed and their livers and spleens were harvested for monitoring bacterial translocation. Tissue suspensions from the harvested organs were then cultured on MacConkey agar plates for 24–48 hr prior to enumeration. Values are mean±standard error. Significant differences (ANOVA, the SAS program) from the control: *$P<0.05$.

Both the *B. lactis* HN019 and *L. rhamnosus* HN001 supplemented mice showed significantly lower levels of bacterial translocation into the liver and spleen than the *S. typhimurium* alone fed mice (FIG. 3).

Figure 4:
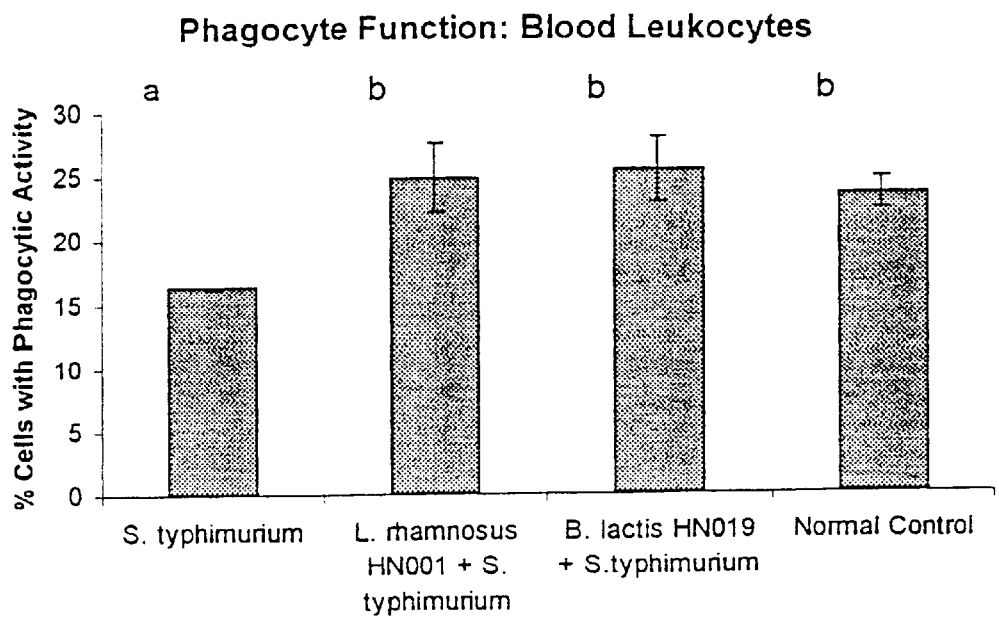
FIG. 4 shows the effect of supplementation of mice with *L. rhamnosus* HN001 or *B. lactis* HN019 on the phagocytic activity of peripheral blood leukocytes from mice challenged with *S. typhimurium* as described in example 8. Unsupplemented and *B. lactis* HN019, or *L. rhamnosus* HN001 supplemented BALB/c mice were orally challenged with *S. typhimurium* following continuous daily supplementation. Phagocytic activity of peripheral blood leukocytes was determined six days after challenge using flow cytometry and fluoroscein isothiocyanate-labelled *Escherichia coli*. Values are mean±standard error. Values (mean±standard error) with different superscripts are significantly different (ANOVA, the SAS program): $P<0.01$.

Challenge infection resulted in a significant suppression of phagocyte function (FIG. 4); the phagocytic activity of control mice challenged with *S. typhimurium* was significantly lower than that of the uninfected mice. However, infection with *S. typhimurium* had no effect on the phagocytic ability of peripheral blood leukocytes of mice supplemented with *B. lactis* HN019 or *L. rhamnosus* HN001 . This was shown by similar levels of phagocytic activity in mice supplemented with *B. lactis* HN019 or *L. rhamnosus* HN001 and challenged with *S. typhimurium* and the normal uninfected control mice.

Figure 5:
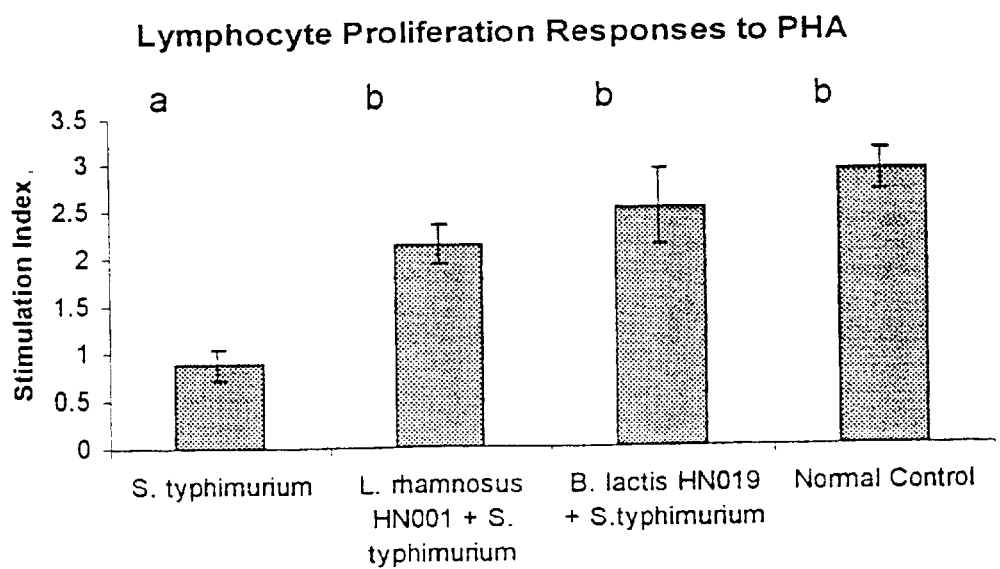
FIG. 5 shows the effect of supplementation of mice with *L. rhamnosus* HN001 or *B. lactis* HN019 on the proliferative responses of spleen lymphocytes from mice challenged with S. typhimuritim as described in example 8. Unsupplemented and *B. lactis* HN019, or *L. rhamnosus* HN001 supplemented BALB/c mice were orally challenged with *S. typhimurium* following continuous daily supplementation. Six days after challenge the proliferative responses of spleen lymphocytes were measured colourimetrically following the incorporation of 5-bromo-2'-debxyuridine for the final 16 hrs of the 96 hr incubation. Values (mean±standard error) with different superscripts are significantly different (ANOVA, the SAS program): $P<0.01$).

Both the *B. lactis* HN019 and *L. rhamnosus* HN001 supplemented mice showed higher lymphocyte proliferative responses to PHA than the *S. typhimurium* challenged control (FIG. 5). There was no significant difference in the response between mice receiving *B. lactis* HN019 or *L. rhamnosus* HN001 and the uninfected control mice.

Together these results suggest that supplementation with *B. lactis* HN019 or *L. rhamnosus* HN001 is able to confer protection against enteric pathogens such as *Salmonella typhimurium*. Enhanced resistance to infection is accompanied by an increase in immune performance.

What is claimed is:

1. A biologically pure culture of either *Lactobacillus* (*L.*) *rhamnosus* HN001 AGAL deposit number NM07/09514 or *Lactobacillus* (*L.*) *rhamnosus* HN067 AGAL deposit number NM97/01925.

2. A composition comprising at least one of the strains selected from the group consisting of *L. rhamnosus* HN001 AGAL deposit number NM97/09514, *L. rhamnosus* HN067 AGAL deposit number NM97/01925, *Bifidobacterium* (*B.*) *lactis* HN019 AGAL deposit number NM97/09513 and *L. acidophilus* HN017 AGAL deposit number NM97/09515, in an amount effective to stimulate an immune response, and a physiologically acceptable excipient or diluent.

3. The composition as claimed in claim 2 comprising at least two or more of said strains.

4. The composition as claimed in claim 2 wherein said physiologically acceptable excipient or diluent is a food.

5. The composition as claimed in claim 4 wherein said food is selected from the group consisting of cultured milk, yoghurt, cheese, milk drink and milk powder.

6. The composition as claimed in claim 2 wherein said physiologically acceptable excipient or diluent is also a pharmacologically acceptable excipient or diluent.

7. A physiologically acceptable pure culture of a strain, homologue, or mutant of at least one of the strains selected from the group consisting of:

*L. acidophilus* HN017,
*L. rhamnosus* HN001,
*B. lactis* HN019, and
*L. acidophilus* HN067, having all of the identifying characteristics of said strains.

8. A method of enhancing natural and acquired immunity which comprises administering to a mammal in need thereof at least one a biologically pure culture of a strain of claim 1 or claim 7 in an amount effective to stimulate an immune response.

9. The method of claim 8 wherein two or more of the strains are administered.

10. A method of enhancing natural and acquired immunity which comprises administering to a mammal in need thereof a therapeutically effective amount of the composition of claim 2.

11. The method of claim 8 wherein said physiologically acceptable excipient or diluent is a food.

12. The method of claim 11 wherein said food is selected from the group consisting of cultured milk, yoghurt, cheese, milk drink and milk powder.

* * * * *

UNITED STATES PATENT AND TRADEMARK OFFICE
CERTIFICATE OF CORRECTION

PATENT NO. : 6,379,663 B1
DATED : April 30, 2002
INVENTOR(S) : Harsharnjit S. Grill et al.

It is certified that error appears in the above-identified patent and that said Letters Patent is hereby corrected as shown below:

<u>Column 14,</u>
Line 67, delete "L. acidophilus HN067" and insert therefor -- L. rhamnosus HN067 --.

Signed and Sealed this

Eighth Day of July, 2003

JAMES E. ROGAN
*Director of the United States Patent and Trademark Office*